US011877883B2

(12) United States Patent
Cheng et al.

(10) Patent No.: US 11,877,883 B2
(45) Date of Patent: Jan. 23, 2024

(54) BIOLOGICAL SOUND DETECTION DEVICE

(71) Applicants: DENSO CORPORATION, Kariya (JP); TOYOTA JIDOSHA KABUSHIKI KAISHA, Toyota (JP); MIRISE Technologies Corporation, Nisshin (JP)

(72) Inventors: Fan Cheng, Nisshin (JP); Yuki Anno, Nisshin (JP); Yoshinori Tsuchiya, Nisshin (JP)

(73) Assignees: DENSO CORPORATION, Kariya (JP); TOYOTA JIDOSHA KABUSHIKI KAISHA, Toyota (JP); MIRISE Technologies Corporation, Nisshin (JP)

( * ) Notice: Subject to any disclaimer, the term of this patent is extended or adjusted under 35 U.S.C. 154(b) by 0 days.

(21) Appl. No.: 17/879,056

(22) Filed: Aug. 2, 2022

(65) Prior Publication Data
US 2023/0042847 A1 Feb. 9, 2023

(30) Foreign Application Priority Data
Aug. 4, 2021 (JP) ................. 2021-128458

(51) Int. Cl.
*A61B 7/04* (2006.01)
(52) U.S. Cl.
CPC ........ *A61B 7/04* (2013.01); *A61B 2562/0204* (2013.01)
(58) Field of Classification Search
CPC ........................ A61B 7/04; A61B 2562/0204
See application file for complete search history.

(56) References Cited

U.S. PATENT DOCUMENTS 9,462,995 B2 * 10/2016 Nakamura ............... B06B 1/06
2007/0113649 A1 5/2007 Bharti et al.
2016/0367213 A1 12/2016 Fujita et al.

FOREIGN PATENT DOCUMENTS

DE 102018103396 A1 * 8/2019

OTHER PUBLICATIONS

Haixia Li et al., "Design of a high SNR electronic heart sound sensor based on a MEMS bionic hydrophone"(online), AIP Advances 9, 015005 (2019), (URL : https://doi.org/10.1063/1.5062619).

* cited by examiner

*Primary Examiner* — Andrew L Sniezek
(74) *Attorney, Agent, or Firm* — POSZ LAW GROUP, PLC

(57) ABSTRACT

A biological sound detection device includes a housing, a medium, a transducer unit, a detection unit, and a pressure adjusting unit. The medium has an acoustic impedance closer to water than air. The transducer unit is arranged in the housing, and converts a biological sound transmitted through the medium into an electric signal. The detection unit provides, together with the housing, an accommodation region that accommodates the medium, detects the biological sound, transmits the biological sound to the medium, and is deformable in a direction approaching the transducer unit according to a load of a physical body. The pressure adjusting unit adjusts a pressure of the medium so as to suppress an increase in the pressure of the medium due to deformation of the detection unit.

3 Claims, 8 Drawing Sheets

BIOLOGICAL SOUND DETECTION DEVICE

CROSS REFERENCE TO RELATED APPLICATION

This application is based on Japanese Patent Application No. 2021-128458 filed on Aug. 4, 2021, the disclosure of which is incorporated herein by reference.

TECHNICAL FIELD

The present disclosure relates to a biological sound detection device.

BACKGROUND

An electronic heart sound sensor, that is, a biological sound detection device has been proposed.

SUMMARY

The present disclosure provides a biological sound detection device. The biological sound detection device includes a housing, a medium, a transducer unit, and a detection unit. The medium has an acoustic impedance closer to water than air. The transducer unit is arranged in the housing, and converts a biological sound transmitted through the medium into an electric signal. The detection unit provides, together with the housing, an accommodation region that accommodates the medium, detects the biological sound, transmits the biological sound to the medium, and is deformable in a direction approaching the transducer unit according to a load of a physical body.

BRIEF DESCRIPTION OF DRAWINGS

The features and advantages of the present disclosure will become more apparent from the following detailed description made with reference to the accompanying drawings. In the drawings.

DETAILED DESCRIPTION

Figure 1:
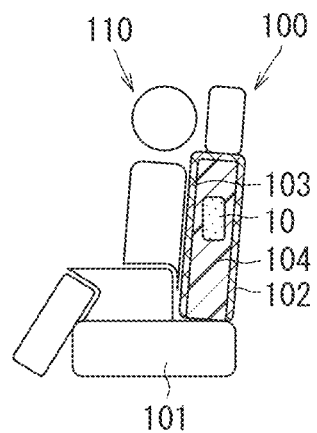
FIG. 1 is a diagram showing an arrangement of a biological sound detection device according to a first embodiment.

For example, in an exemplary biological sound detection device, a SN ratio, that is, a detection sensitivity of biological sound is increased by filling a housing with a medical coupling agent as a medium. However, depending on an external force (load) received from a physical body, the biological sound cannot be detected with high sensitivity. For this reason and other reasons that are not described, further improvement is required to be made in the biological sound detection device.

The disclosure of Non-Patent Literature 1 is incorporated herein by reference as an explanation of technical elements in the present disclosure.

[Non-Patent Literature 1] H. Li et al., "Design of a high SNR electronic heart sound sensor based on a MEMS bionic hydrophone", [online], AIP Advances 9, 015005 (2019), (URL: https://doi.org/10.1063/1.5062619)

The present disclosure provides a biological sound detection device capable of detecting biological sound with high sensitivity regardless of a load of a physical body.

An exemplary embodiment of the present disclosure provides a biological sound detection device that includes a housing, a medium, a transducer unit, a detection unit, and a pressure adjusting unit. The medium has an acoustic impedance closer to water than air. The transducer unit is arranged in the housing, and converts a biological sound transmitted through the medium into an electric signal. The detection unit provides, together with the housing, an accommodation region that accommodates the medium, detects the biological sound, transmits the biological sound to the medium, and is deformable in a direction approaching the transducer unit according to a load of a physical body. The pressure adjusting unit adjusts a pressure of the medium so as to suppress an increase in the pressure of the medium due to deformation of the detection unit.

In the exemplary embodiment of the present disclosure, the medium having an acoustic impedance close to that of water is arranged in the accommodation region. The biological sound is transmitted from the detection unit to the transducer unit via the medium. This configuration can reduce the reflection loss in the propagation path from the physical body to the transducer unit, particularly in the propagation path from the detection unit to the transducer unit.

Further, the pressure adjusting unit can suppress the pressure increase of the medium due to the deformation of the detection unit. This configuration can suppress change in the density of the medium due to the load, and change in the acoustic impedance of the medium. As a result, it is possible to provide a biological sound detection device capable of detecting biological sound with high sensitivity regardless of the load of the physical body.

Hereinafter, multiple embodiments will be described with reference to the drawings. The same or corresponding elements are designated with the same reference numerals throughout the embodiments, and descriptions thereof will not be repeated. When a part of the features in each embodiment is explained, the remaining part of the features may be provided by the features in other prior explained embodiments. Further, it is possible to not only combine configurations as specified in the description of the embodiments but also partially combine configurations of embodiments even though not specified herein as long as the combination does not cause difficulty.

First Embodiment

First, the arrangement of the biological sound detection device according to the present embodiment will be described with reference to FIG. 1. FIG. 1 is a partial cross-sectional view.

(Arrangement of Biological Sound Detection Device)

The biological sound detection device may be arranged in a sheet of a moving object. The moving object includes a vehicle, a flying object, a ship, a construction machinery, and the like.

As shown in FIG. 1, a seat 100 of the moving object includes a seating portion 101 and a backrest 102. The seating portion 101 supports the buttock, thigh, and the like of an occupant 110 who is seated on the seat 100. The backrest 102 supports the back of the occupant 110.

The backrest 102 has a skin member 103 and a seat pad 104. The skin member 103 covers the seat pad 104 and forms a backrest surface of the backrest 102. The backrest surface is a surface on the seat 100 where the back of the seated occupant can come into contact. As the skin member 103, for example, leather, fabric, or the like can be used.

The seat pad 104 is made of an elastically deformable material, such as urethane. The seat pad 104 is a cushion member that supports the occupant 110. Similarly to the backrest 102, the seating portion 101 also has a skin member and a seat pad (not shown).

The biological sound detection device 10 of the present embodiment is arranged inside, for example, the backrest 102. The whole or a part of the biological sound detection device 10 is covered with the seat pad 104. The biological sound detection device 10 detects the biological sound of the occupant 110. The occupant 110 corresponds to a physical body. Biological sounds are acoustic signals generated from each part of the physical body. The biological sound detected by the biological sound detection device 10 is at least one of general biological sounds such as a heart sound, a sound of an organ other than the heart (for example, lung sound), a breath sound, and a blood flow sound (for example, a heart ballot which is the blood flow of an artery). The biological sound detection device 10 detects, for example, the heart sounds of the occupant 110 via the members constituting the seat 100.

(Structure of Biological Sound Detection Device)

Figure 2:
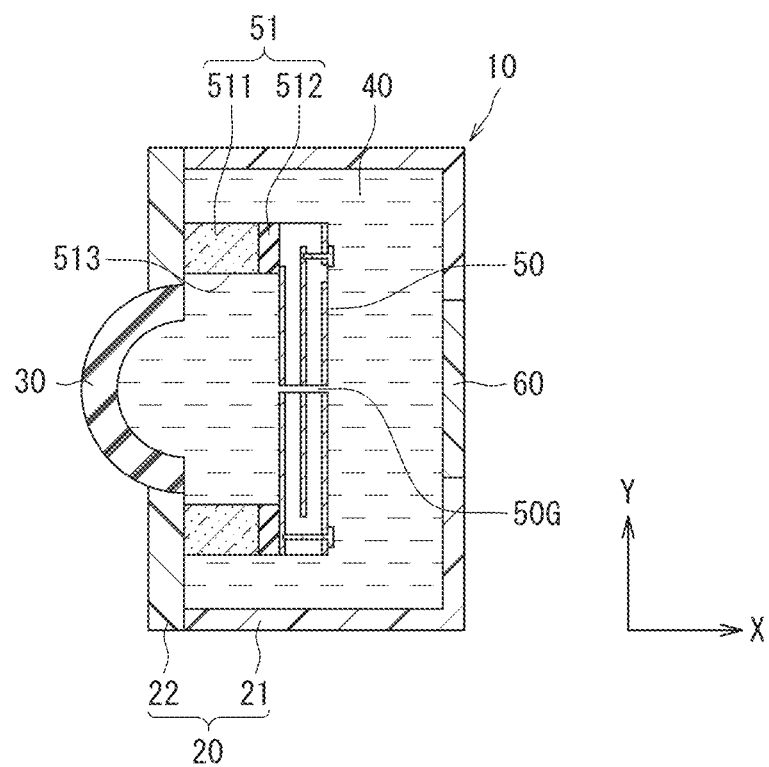
FIG. 2 is a cross-sectional view showing the biological sound detection device.

Next, the structure of the biological sound detection device will be described with reference to FIG. 2. FIG. 2 is a cross-sectional view showing a biological sound detection device. FIG. 2 shows a state in which the load of the occupant 110 is not applied.

As shown in FIG. 2, the biological sound detection device 10 includes a housing 20, a detection unit 30, a medium 40, a transducer unit 50, and a pressure adjusting unit 60.

The housing 20 accommodates the transducer unit 50. The housing 20 protects the transducer unit 50. The constituent material of the housing 20 is not particularly limited. The housing 20 is made of, for example, metal, ceramic, glass, resin, or the like. The housing 20 of the present embodiment has a case 21 and a cover 22. The case 21 has a box shape whose one surface is open. The cover 22 is provided so as to close a part of the opening of the case 21. The cover 22 may be referred to as a lid.

The detection unit 30 provides, together with the housing 20, an accommodation region (accommodation space) for accommodating the medium 40. The accommodation region may be referred to as an arrangement area in which the medium 40 is arranged. The detection unit 30 and the housing 20 are wall members that define the accommodation region. The detection unit 30 is provided on the housing 20. The detection unit 30 is fixed to the housing 20. The detection unit 30 of this embodiment is provided on the cover 22. The detection unit 30 is provided so as to close the opening of the cover 22.

The accommodation region provided by the detection unit 30 and the housing 20 is not limited to the above configuration. For example, the housing 20 may have only the case 21, and the detection unit 30 may close the opening of the case 21. That is, the cover 22 may be excluded. The fixed structure between the housing 20 and the detection unit 30 is not particularly limited. If necessary, sealing or the like may be applied in order to hold the medium 40. The fixed structure between the case 21 and the cover 22 is also not particularly limited. If necessary, sealing or the like may be applied.

The detection unit 30 is formed by using a solid material having an acoustic impedance closer to that of water than the constituent material of the housing 20. The detection unit 30 may use a material having an acoustic impedance that substantially matches water. Specifically, it is preferable to use a material in which the ratio of the acoustic impedance to water is in the range of 0.5 to 5. More preferably, it is preferable to use a material in which the ratio of the acoustic impedance to water is in the range of 0.8 to 2. This configuration can reduce the reflection loss at the interface of the detection unit 30.

The detection unit 30 of this embodiment is formed by using silicone rubber. The acoustic impedance of the silicone rubber is $1.44 \times 10^6$ kg/(s·m$^2$). The acoustic impedance of water is $1.53 \times 10^6$ kg/(s·m$^2$). When the housing 20 is made of metal, for example, its acoustic impedance is 10 times or more that of water. As a result, the biological sound is detected by the detection unit 30 and reflected by the housing 20. The biological sound is transmitted to the medium 40 in the accommodation region through the detection unit 30. In this way, the detection unit 30 detects the biological sound and transmits the biological sound to the medium 40.

The detection unit 30 is deformable in a direction approaching to the transducer unit 50 according to the load of the occupant 110 (physical body). The detection unit 30 of the present embodiment is arranged so as to be aligned with the transducer unit 50 in the X direction. In a plan view in the X direction, the detection unit 30 is arranged so as to overlap with at least a part of the transducer unit 50. The detection unit 30 is configured to be able to bend in the X direction under a load, that is, to be elastically deformable. The larger the load, the closer the detection unit 30 approaches to the transducer unit 50.

The detection unit 30 protrudes to the outside of the accommodation region with respect to the cover 22 having a flat plate-shape in a state where the load of the occupant 110 is not applied. The detection unit 30 protrudes from the cover 22 to the side opposite to the transducer unit 50 in the X direction. As a result, when the occupant 110 is seated on the seat 100, the load of the occupant 110 is likely to be applied to the detection unit 30 instead of the housing 20. That is, the biological sound detection device 10 has a structure in which the biological sound of the occupant 110 can be easily detected by the detection unit 30. The inside of the detection unit 30 has a recessed shape. The medium 40 is also arranged in the recess of the detection unit 30.

The medium 40 is arranged in the accommodating area. The medium 40 covers the transducer unit 50. The medium 40 is in contact with the inner surface of the housing 20 and the inner surface of the detection unit 30. The medium 40 is arranged in the propagation path between the detection unit 30 and the transducer unit 50. The medium 40 transmits the biological sound input via the detection unit 30 to the transducer unit 50. In the present embodiment, the medium 40 is filled in almost the entire inside of the housing 20.

The medium 40 has an acoustic impedance closer to water than air. The medium 40 has an acoustic impedance larger than that of air and smaller than that of the material constituting the housing 20. The medium 40 may have an acoustic impedance that closely matches water. Specifically, it is preferable to use a material in which the ratio of the acoustic impedance to water is in the range of 0.5 to 5. More preferably, it is preferable to use a material in which the ratio of the acoustic impedance to water is in the range of 0.8 to 2. As a result, the configuration can reduce the reflection loss at the interface between the detection unit 30 and the medium 40, that is, the reflection loss in the propagation path of the biological sound (acoustic signal) from the detection unit 30 to the transducer unit 50.

As the medium 40, for example, a liquid material such as water or silicone oil, or a solid material such as ultrasonic gel or silicone rubber can be used. The acoustic impedance of the silicone oil is $1.41 \times 10^6$ kg/(s·m$^2$). The acoustic impedance of the ultrasonic gel is $1.41 \times 10^6$ kg/(s·m$^2$). The acoustic impedances of water and silicone rubber are as described above. In this embodiment, water is used as the medium 40. The acoustic impedance of air is $4.39 \times 10^2$ kg/(s·m$^2$).

The transducer unit 50 converts the biological sound into an electric signal. The transducer unit 50 of the present embodiment converts the biological sound transmitted through the medium 40 into an electric signal. The transducer unit 50 is covered with the medium 40. The transducer unit 50 is embedded in, for example, the medium 40 made of a liquid material.

The transducer unit 50 has an element that converts the biological sound into an electric signal. The element is not particularly limited. It may be a resistance change type element or a capacitance change type element. A piezoelectric element that generates an electromotive force may be used. The element is formed using MEMS technology. The MEMS is an abbreviation for Micro Electro Mechanical Systems. By using the MEMS technology, a small transducer unit 50 can be formed. The element is designed to suitably detect a signal of a predetermined frequency, for example, a heart sound.

The transducer unit 50 is fixed to the cover 22 of the housing 20 via a support 51. The support 51 has, for example, a base 511 and an insulating layer 512 interposed between the base 511 and the transducer unit 50. For example, the base 511 is made of silicon and the insulating layer 512 is made of silicon oxide. The support 51 has a through hole 513 that penetrates the base 511 and the insulating layer 512 in the X direction. The transducer unit 50 is partitioned by a gap 50G and is cantilevered by a support 51. The transducer unit 50 covers the opening on the transducer unit 50 side in the through hole 513. The support 51 has an annular shape in a plan view from the X direction. In a plan view from the X direction, the through hole 513 includes the detection unit 30.

The pressure adjusting unit 60 adjusts the pressure of the medium 40 so as to suppress the pressure increase of the medium 40 due to the deformation of the detection unit 30. The details of the pressure adjusting unit 60 will be described later.

(Pressure Adjusting Unit)

Next, the pressure adjusting unit 60 will be described with reference to FIGS. 2, 3, and 4.

When the biological sound detection device 10 does not include the pressure adjusting unit 60, the detection unit 30 approaches the transducer unit 50 by receiving the load (external force) of the occupant 110, so that the volume of the accommodation region of the medium 40 is reduced. As a result, the pressure of the medium 40 rises. As the pressure rises, the density of the medium 40 increases. In this way, the density of the medium 40 changes based on the load. That is, the density of the medium 40 and the acoustic impedance may change based on weight of the occupant 110, a sitting position, posture, and the like.

On the other hand, the biological sound detection device 10 of the present embodiment includes the pressure adjusting unit 60. As shown in FIG. 2, the pressure adjusting unit 60 provides the accommodation region for the medium 40 together with the housing 20 and the detection unit 30. The medium 40 is arranged (accommodated) in the area defined by the housing 20, the detection unit 30, and the pressure adjusting unit 60. The pressure adjusting unit 60 adjusts the pressure of the medium 40 by expanding the accommodation region.

The pressure adjusting unit 60 is provided in the case 21 of the housing 20. The pressure adjusting unit 60 is, for example, a diaphragm (thin-walled portion) provided so as to be deformable with respect to the housing 20, or a membrane (thin film) provided so as to close the opening of the case 21. The pressure adjusting unit 60 expands the accommodation region by deformation. For example, the pressure adjusting unit 60 is deformable so that the pressure of the medium 40 becomes substantially constant regardless of the load of the occupant 110, that is, regardless of the degree of deformation of the detection unit 30.

Figure 3:
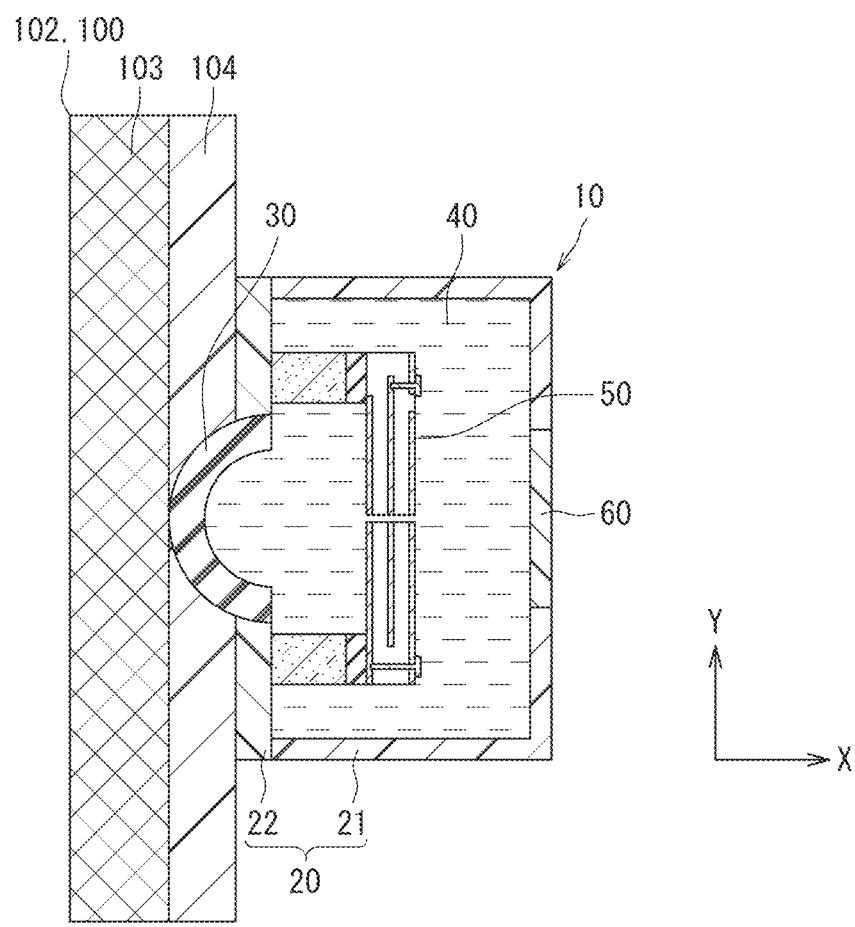
FIG. 3 is a diagram showing a state in which a load of an occupant is not applied.

FIG. 3 shows a state in which the load of the occupant 110 is not applied. As an example, the biological sound detection device 10 of the present embodiment is arranged so that the protruding tip of the detection unit 30 comes into contact with the inner surface of the skin member 103.

In the state before the occupant 110 is seated on the seat 100, the load of the occupant 110 is not applied to the detection unit 30. Therefore, the detection unit 30 is not deformed in the direction approaching the transducer unit 50, and is held at an initial position. Since the detection unit 30 is not deformed, the pressure of the medium 40 does not increase due to the deformation. Therefore, the pressure adjusting unit 60 is not deformed and is held in an initial position. The pressure adjusting unit 60 is, for example, substantially flat.

Figure 4:
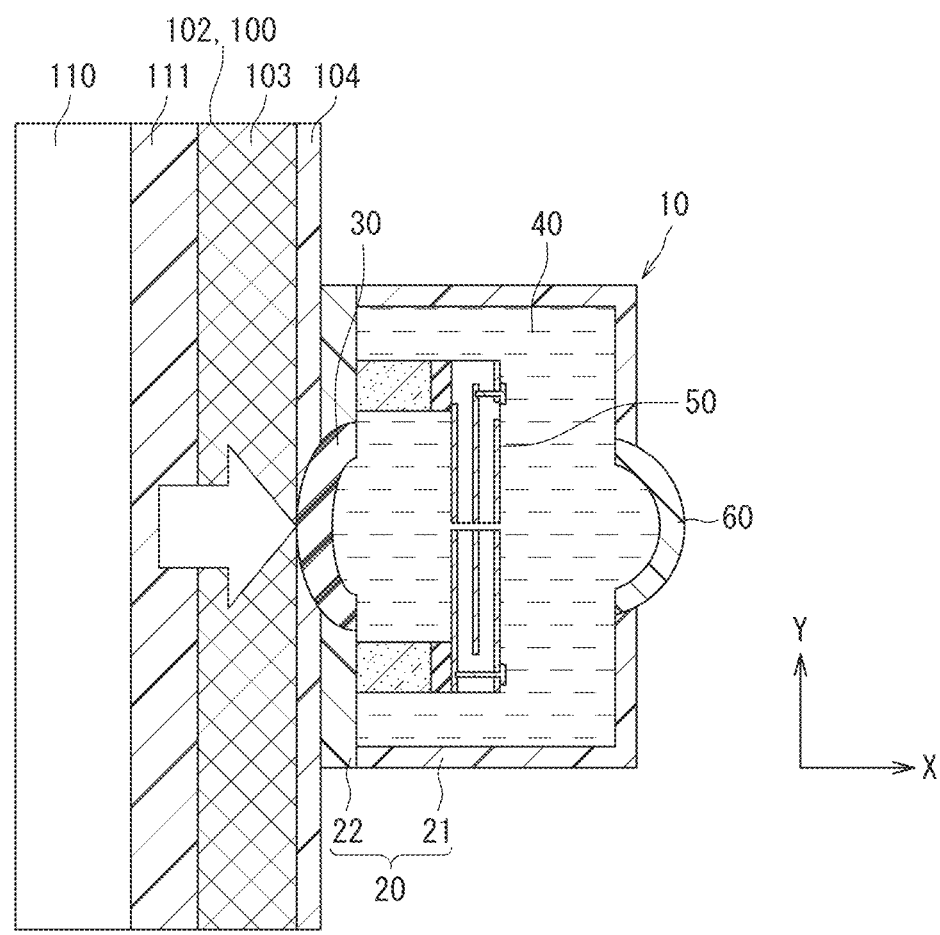
FIG. 4 is a diagram showing a state in which a load of an occupant is applied.

FIG. 4 shows a state in which the load of the occupant 110 is applied. In FIG. 4, the load, that is, the external force received from the occupant 110 is indicated by a white arrow. As shown in FIG. 4, the load of the occupant 110 acts on the detection unit 30 via clothes 111 of the occupant 110 and the skin member 103 of the seat 100.

The detection unit 30 is deformed in the direction approaching the transducer unit 50 according to the load of the occupant 110. The detection unit 30 approaches the transducer unit 50 in the X direction by receiving the load and bending. The detection unit 30 is deformed in a direction of reducing the volume of the accommodation region for the medium 40 with respect to an initial state before the load is applied as shown in FIG. 3. On the other hand, the pressure adjusting unit 60 is deformed so as to suppress the pressure increase of the medium 40 due to the deformation of the detection unit 30. The pressure adjusting unit 60 expands the accommodation region for the medium 40 by deformation, thereby suppressing the pressure rise of the medium 40.

The pressure adjusting unit 60 of the present embodiment deforms according to the load so that the pressure of the medium 40 becomes substantially constant regardless of the load of the occupant 110, that is, regardless of the degree of deformation of the detection unit 30. The pressure adjusting unit 60 is deformed so that the area to be expanded is increased according to the load. As a result, change in the density of the medium 40, that is, the acoustic impedance is suppressed.

The acoustic impedance of the occupant 110, that is, the human body, is almost equal to that of water. The acoustic impedance of the human body is $1.99 \times 10^6$ kg/(s·m$^2$). The acoustic impedance of clothes 111, for example nylon, is $2.91 \times 10^6$ kg/(s·m$^2$). The acoustic impedance of the skin member 103 of the seat 100, which may be provided by cowhide, is $1.41 \times 10^6$ to $1.71 \times 10^6$ kg/(s·m$^2$).

As described above, the acoustic impedance of the clothes 111 and the skin member 103 is close to the acoustic impedance of the human body and water.

The acoustic impedance of each of the occupant 110, the clothes 111, the skin member 103, the detection unit 30, and the medium 40 is in the range of 0.8 to 2 in the ratio of the acoustic impedance to water. Therefore, this configuration can reduce the reflection loss due to the difference in acoustic impedance in the propagation path of the biological sound, for example, the heart sound from the occupant 110 to the transducer unit 50.

When the occupant 110 leaves the seat 100, that is, when the load is released, the detection unit 30 recovers from the deformed state and returns to the initial position. The pressure adjusting unit 60 also returns to the initial position.

(Pressure of Medium and Signal Strength)

Next, the relationship between the pressure of the medium 40 and the signal strength will be described with reference to FIG. 5. "No pressurization" shown in FIG. 5 indicates the signal intensity in a state where water, which is the medium 40, is not pressurized. "Pressurization" indicates the signal strength in the state where water is pressurized. The pressure of water with pressurization is higher than the pressure of water without pressurization.

Figure 5:
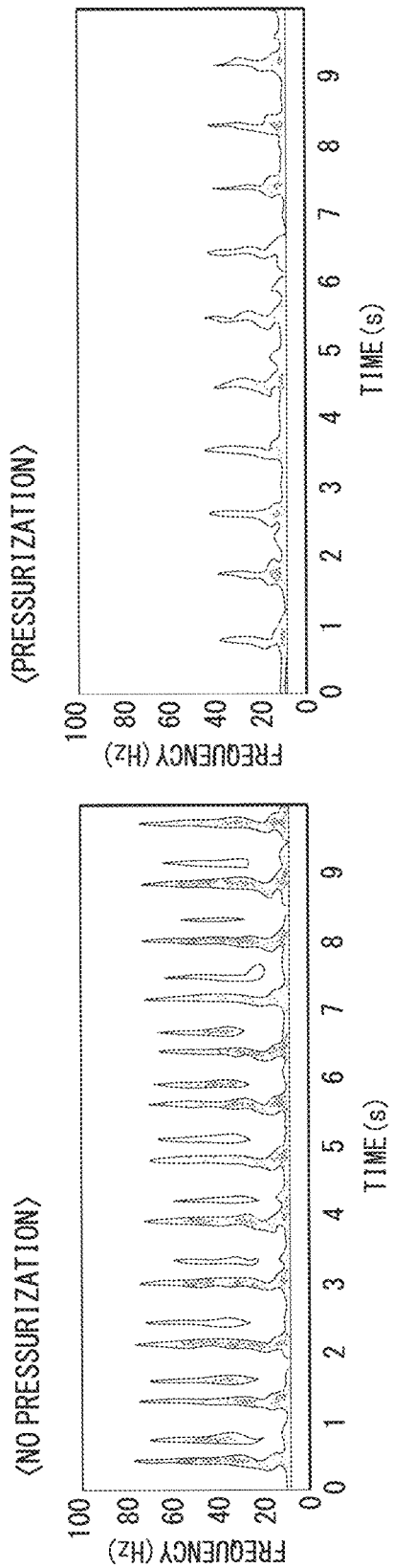
FIG. 5 is a diagram showing a relationship between pressure of a medium and signal intensity.

As shown in FIG. 5, when water is pressured, that is, when the pressure of the medium 40 is high, the signal strength at 30 to 70 Hz decreases with respect to the case where water is not pressured. This is because the acoustic impedance of the medium 40 (water) is increased by pressurization, and the transmission characteristics in the high frequency range (30 Hz or higher) are weakened with respect to the low frequency range. When the pressure of the medium 40 becomes high, the detection sensitivity of the biological sound decreases.

Summary of First Embodiment

According to the biological sound detection device 10 of the present embodiment, the medium 40 having an acoustic impedance close to that of water is arranged in the accommodation region. The biological sound is transmitted from the detection unit 30 to the transducer unit 50 via the medium 40. This configuration can reduce the reflection loss in the propagation path from the physical body to the transducer unit 50. In particular, it is possible to reduce the reflection loss at the interface in the propagation path from the detection unit 30 to the transducer unit 50. As a result, the intensity of the biological sound (acoustic signal) detected by the transducer unit 50 can be increased, and the biological sound can be detected even in a noise environment of a moving object such as running noise.

Further, the pressure adjusting unit 60 can suppress the pressure increase of the medium 40 due to the deformation of the detection unit 30. This configuration can suppress changes in the density of the medium 40 due to the load, and changes in the acoustic impedance of the medium 40. As a result, the biological sound can be detected with high sensitivity regardless of the load of the occupant 110 (physical body).

In the pressure adjusting unit 60 of the present embodiment, the housing 20 together with the detection unit 30 provides the accommodation region for the medium 40. The pressure adjusting unit 60 expands the accommodation region of the medium 40 by deformation so as to suppress the pressure increase of the medium 40. As a result, the biological sound can be detected with high sensitivity regardless of the load of the occupant 110.

In particular, in the present embodiment, the pressure adjusting unit 60 deforms according to the load so that the pressure of the medium 40 becomes substantially constant regardless of the load of the occupant 110, that is, regardless of the degree of deformation of the detection unit 30. Since the pressure of the medium 40 is kept substantially constant by the pressure adjusting unit 60, the detection sensitivity of the biological sound can be further increased.

Modifications

Figure 6:
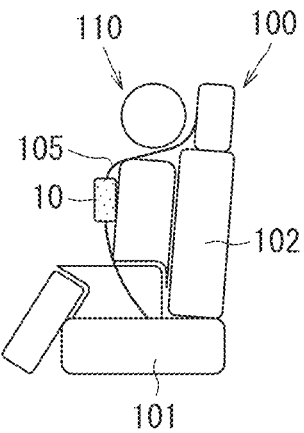
FIG. 6 is a diagram showing a modification.

An example is shown in which the biological sound detection device 10 is arranged in the backrest 102 of the seat 100, but the present disclosure is not limited thereto. For example, as shown in FIG. 6, the seat belt 105 may be provided with the biological sound detection device 10. Although not shown, the biological sound detection device 10 may be provided in the seating portion 101 of the seat 100. FIG. 6 is a diagram showing a biological sound detection device according to a modification. FIG. 6 corresponds to FIG. 1.

An example is shown in which the pressure adjusting unit 60 is deformed so as to keep the pressure of the medium 40 substantially constant regardless of the load, but the present disclosure is not limited thereto. For example, when the pressure of the medium 40 rises with the deformation of the detection unit 30, and the pressure adjusting unit 60 may be deformed to expand the accommodation region when the pressure of the medium 40 exceeds a predetermined threshold value. By expanding the accommodation region, it is possible to suppress an increase in pressure of the medium 40. The pressure adjusting unit 60 may be deformed to expand the accommodation region at least when a load is applied.

An example is shown in which the biological sound detection device 10 is arranged so that the protruding tip of the detection unit 30 comes into contact with the inner surface of the skin member 103, but the present disclosure is not limited thereto. The biological sound detection device 10 may be arranged so that the tip of the detection unit 30 comes into contact with the seat pad 104 on the backrest surface side. That is, the biological sound may be detected via the skin member 103 and the seat pad 104. The acoustic impedance of the urethane constituting the seat pad 104 is, for example, $1.23 \times 10^5$ kg/(s·m$^2$). In this case, the reflection loss at the interface of the seat pad 104 is about several dB. In order to reduce the reflection loss at the interface of the seat pad 104, it is preferable to arrange the detection unit 30 in contact with the skin member 103 as described above.

Second Embodiment

The second embodiment is a modification of the preceding embodiment as a basic configuration and may incorporate description of the preceding embodiment.

Figure 7:
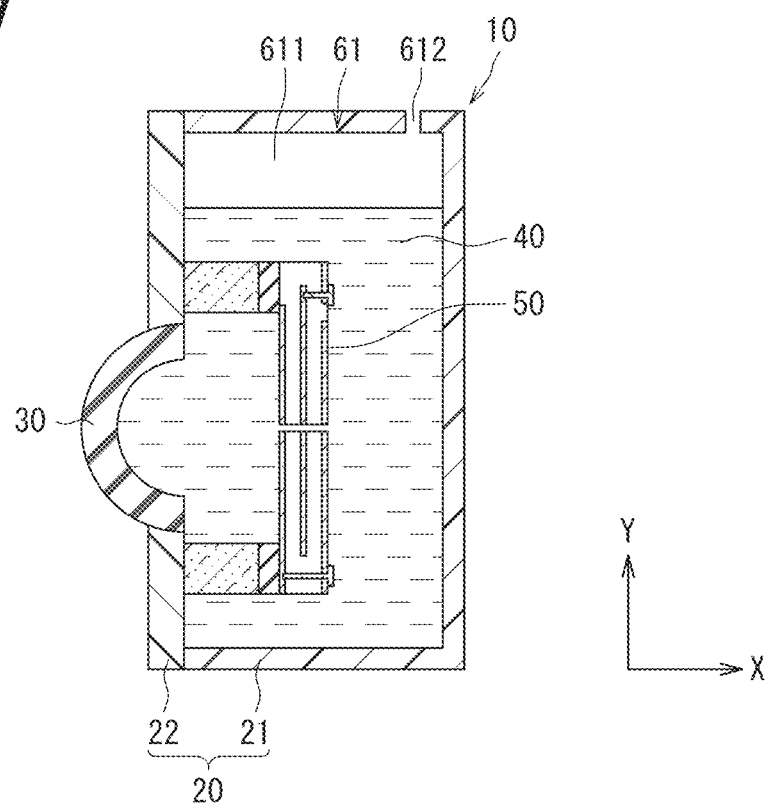
FIG. 7 is a cross-sectional view showing a biological sound detection device according to a second embodiment.

FIG. 7 shows a biological sound detection device 10 of the present embodiment. FIG. 7 is a cross sectional view corresponding to FIG. 2. FIG. 7 shows a state in which the load of the occupant 110 is not applied. The biological sound detection device 10 includes a pressure adjusting unit 61 having an air layer 611 instead of the pressure adjusting unit 60. The air layer 611 is provided adjacently to the medium 40 in the housing 20. The air layer 611, that is, the pressure adjusting unit 61 provides, together with the housing 20 and the detection unit 30, the accommodation region for the medium 40. The air layer 611 defines the accommodation region for the medium 40. The air layer 611 is provided at the end of the housing 20 in the Y direction orthogonal to the X direction.

The pressure adjusting unit 61 further includes a ventilation hole 612. The ventilation hole 612 penetrates the case 21 of the housing 20. The ventilation hole 612 communicate the air layer 611 with the external atmosphere of the housing 20. The pressure adjusting unit 61 may have a filter or the like around the ventilation hole 612, which enables ventilation and hinders the movement of the medium 40. Other configurations are similar to those of the biological sound detection device 10 described in the preceding embodiment.

Figure 8:
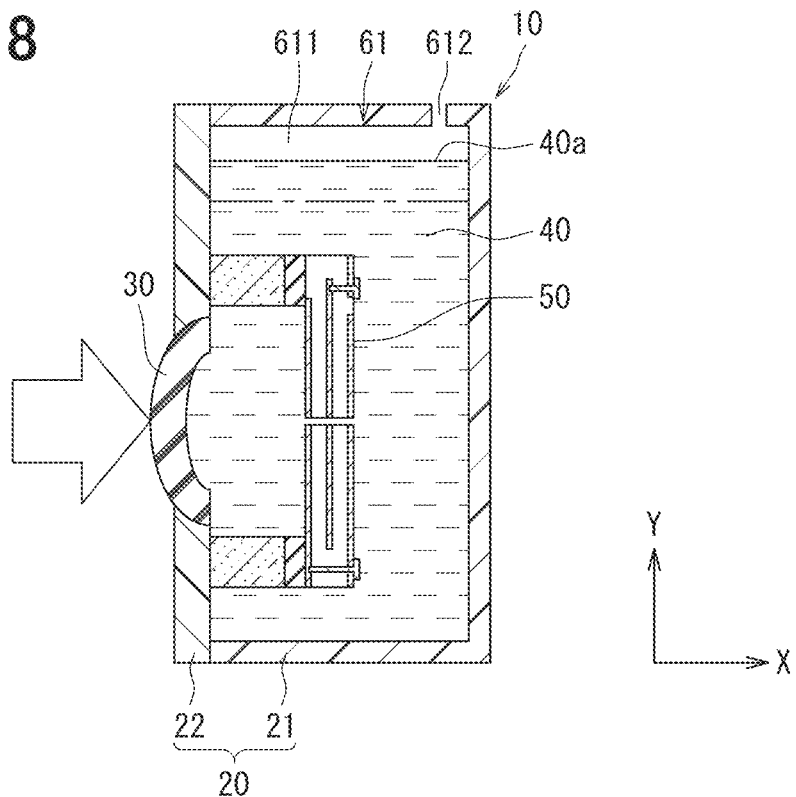
FIG. 8 is a diagram showing a state in which a load of an occupant is applied.

FIG. 8 shows a state in which the load of the occupant 110 is applied. In FIG. 8, for convenience, the members constituting the occupant 110 and the seat 100 are omitted, and the load is indicated by a white arrow. Similarly to the preceding embodiment, the detection unit 30 is deformed in the direction approaching the transducer unit 50 according to the load of the occupant 110. The detection unit 30 approaches the transducer unit 50 in the X direction by receiving the load and bending. The detection unit 30 is deformed in a direction of reducing the volume of the accommodation region of the medium 40.

On the other hand, the pressure adjusting unit 61 suppresses an increase in the pressure of the medium 40 by expanding the accommodation region for the medium 40. The pressure adjusting unit 61 expands the accommodation region by reducing the volume of the air layer 611. The volume of the air layer 611 is reduced as an end face 40a of the medium 40 rises. The dash-dot line shown in FIG. 8 indicates the position of the end face 40a before the load is applied. The volume of the air layer 611 reduces according to the load so that the pressure of the medium 40 becomes substantially constant regardless of the load of the occupant 110, that is, regardless of the degree of deformation of the detection unit 30. As a result, change in the density of the medium 40, that is, the acoustic impedance is suppressed.

When the load is released, the volume of the air layer 611 also returns to the initial state as the detection unit 30 returns from the deformed state to the initial position.

Summary of Second Embodiment

The biological sound detection device 10 according to the present embodiment can achieve the same effect as the configurations described in the preceding embodiment. That is, since the biological sound is transmitted from the detection unit 30 to the transducer unit 50 via the medium 40, it is possible to reduce the reflection loss in the propagation path from the detection unit 30 to the transducer unit 50. The pressure adjusting unit 61 expands the accommodation region by reducing the volume of the air layer 611. With this configuration, the pressure adjusting unit 61 can suppress the pressure increase of the medium 40 due to the deformation of the detection unit 30. As a result, the biological sound can be detected with high sensitivity regardless of the load of the occupant 110 (physical body).

The volume of the air layer 611 reduces according to the load so that the pressure of the medium 40 becomes substantially constant regardless of the load of the occupant 110, that is, regardless of the degree of deformation of the detection unit 30. Since the pressure of the medium 40 is kept substantially constant by the pressure adjusting unit 61, the detection sensitivity of the biological sound can be further increased.

In the present embodiment, the above-mentioned effect can be obtained by a simple structure.

Modifications

Figure 9:
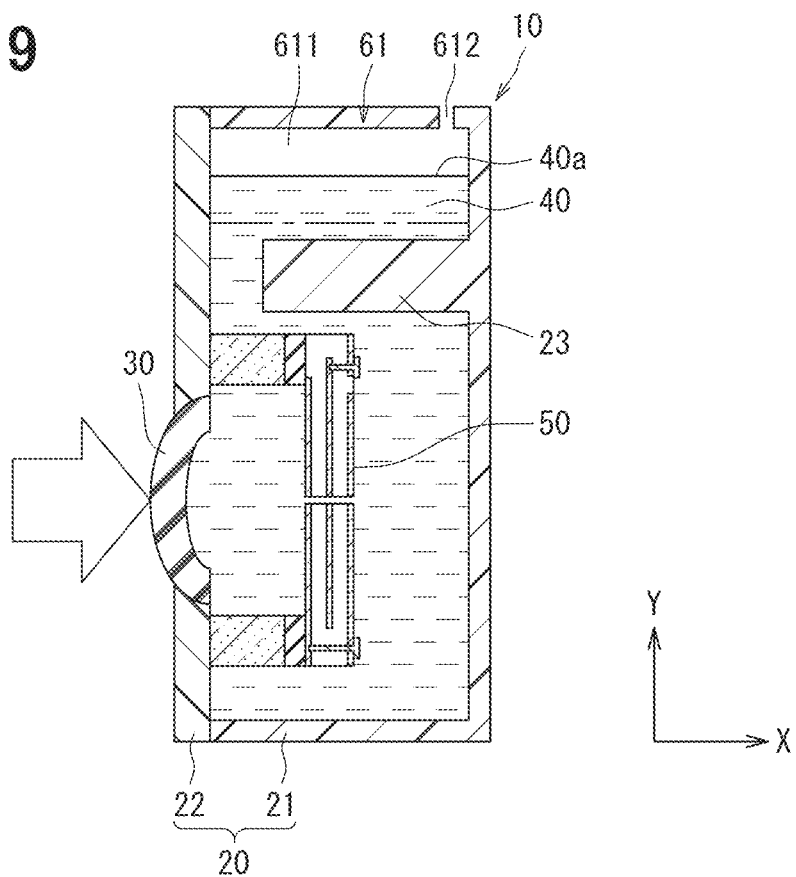
FIG. 9 is a cross-sectional view showing a modification.

As shown in FIG. 9, a partition wall 23 may be provided in the housing 20. The partition wall 23 is provided between the air layer 611 and the transducer unit 50 in the Y direction. The end face 40a of the medium 40 is located on the air layer 611 side with respect to the partition wall 23 before the load is applied, which is indicated by dash-dot line. The partition wall 23 locally narrows the accommodation region for the medium 40. In FIG. 9, the partition wall 23 is provided in the case 21, but the partition wall 23 may be provided in the cover 22. The partition wall 23 may be provided in both the case 21 and the cover 22.

By providing the partition wall 23, the end face 40a is farther from the transducer unit 50 even if the volume of the medium 40 is the same, as compared with the configuration without the partition wall 23. As a result, even if the end face 40a of the liquid, which is the medium 40, that is, the liquid surface shakes due to the vibration of the moving object, the transducer unit 50 is unlikely to be exposed from the medium 40. Therefore, the biological sound can be detected with high sensitivity.

Third Embodiment

The third embodiment is a modification of the preceding embodiments as a basic configuration and may incorporate description of the preceding embodiments.

Figure 10:
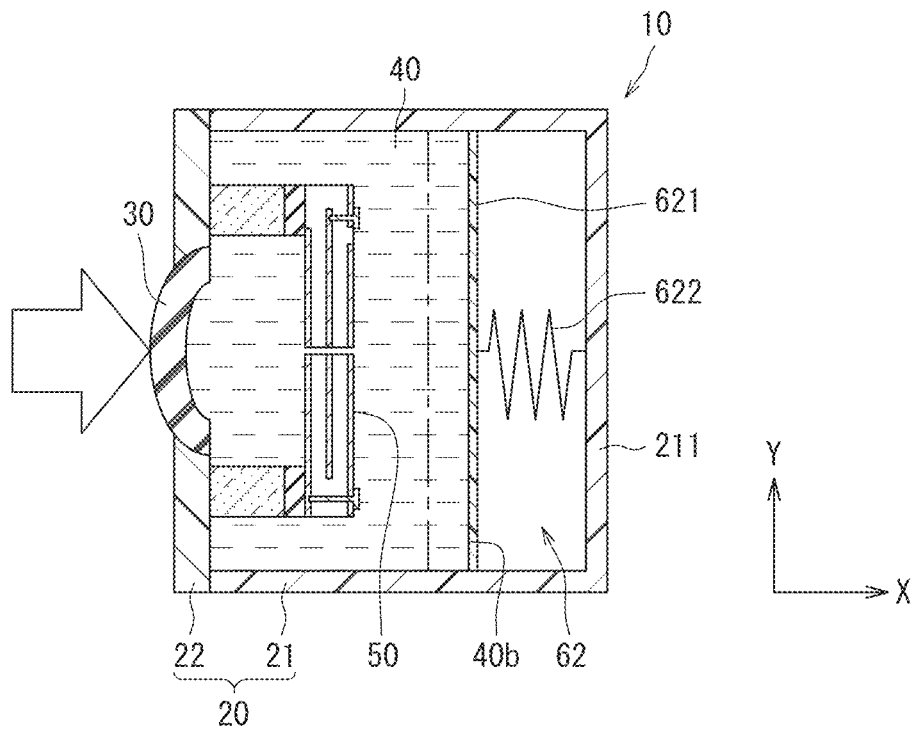
FIG. 10 is a cross-sectional view showing a biological sound detection device according to a third embodiment.

FIG. 10 shows a biological sound detection device 10 of the present embodiment. FIG. 10 shows a state in which the load of the occupant 110 is applied. In FIG. 10, for convenience, the occupant 110 and the seat 100 are omitted, and the load is indicated by a white arrow.

The biological sound detection device 10 includes a pressure adjusting unit 62 having a partition plate 621 and an elastic member 622 instead of the pressure adjusting units 60 and 61. The partition plate 621 is provided adjacently to the medium 40 in the housing 20. The partition plate 621, that is, the pressure adjusting unit 62 provides, together with the housing 20 and the detection unit 30, the accommodation region for the medium 40. The partition plate 621 defines the accommodation region for the medium 40. The partition plate 621 is arranged side by side with the medium 40 in the X direction. The partition plate 621 is in contact with an end face 40b of the medium 40.

The partition plate 621 divides the space in the housing 20 into a region in which the medium 40 is arranged and a region in which the medium 40 is not arranged. The partition plate 621 is attached to the case 21 of the housing 20 so as to be slidable in the X direction.

The elastic member 622 is provided between the partition plate 621 and a bottom wall 211 of the case 21. The bottom wall 211 faces the cover 22 in the X direction. The elastic member 622 is elastically deformable by applying an external force. The elastic member 622 holds the partition plate 621 at a predetermined value in the X direction by the reaction force of the elastic deformation. In this embodiment, a spring is used as the elastic member 622. One end of the spring, which is the elastic member 622, is fixed to the partition plate 621, and the other end is fixed to the bottom wall 211. As the spring, for example, a leaf spring, a coil spring, or the like can be adopted. Instead of the spring, rubber or the like, which is an elastic body, may be adopted. Other configurations are similar to those of the biological sound detection device 10 described in the preceding embodiment.

As shown in FIG. 10, when the load of the occupant 110 acts, the detection unit 30 is deformed in the direction approaching the transducer unit 50 according to the load of the occupant 110. The detection unit 30 approaches the transducer unit 50 in the X direction by receiving the load and bending. The detection unit 30 is deformed in a direction of reducing the volume of the accommodation region of the medium 40.

On the other hand, the pressure adjusting unit 62 suppresses an increase in the pressure of the medium 40 by expanding the accommodation region for the medium 40. The pressure adjusting unit 62 expands the accommodation region by sliding the partition plate 621 so as to release the pressure increase of the medium 40. The dash-dot line shown in FIG. 10 indicates the position of the end face 40b before the load is applied. The partition plate 621 is displaced in the X direction so that the pressure of the medium 40 becomes substantially constant regardless of the load of the occupant 110, that is, regardless of the degree of deformation of the detection unit 30. As a result, change in the density of the medium 40, that is, the acoustic impedance is suppressed.

When the load is released, the elastic member 622 releases the energy of elastic deformation as the detection unit 30 returns from the deformed state to the initial position. As a result, the partition plate 621 returns to the initial position.

Summary of Third Embodiment

The biological sound detection device 10 according to the present embodiment can achieve the same effect as the configurations described in the preceding embodiments. That is, since the biological sound is transmitted from the detection unit 30 to the transducer unit 50 via the medium 40, it is possible to reduce the reflection loss in the propagation path from the detection unit 30 to the transducer unit 50. Further, the pressure adjusting unit 62 can suppress the pressure increase of the medium 40 due to the deformation of the detection unit 30. As a result, the biological sound can be detected with high sensitivity regardless of the load of the occupant 110 (physical body).

The partition plate 621 is displaced so that the pressure of the medium 40 becomes substantially constant regardless of the load of the occupant 110, that is, regardless of the degree of deformation of the detection unit 30. Since the pressure of the medium 40 is kept substantially constant by the pressure adjusting unit 62, the detection sensitivity of the biological sound can be further increased.

Fourth Embodiment

The fourth embodiment is a modification of the preceding embodiments as a basic configuration and may incorporate description of the preceding embodiments.

Figure 11:
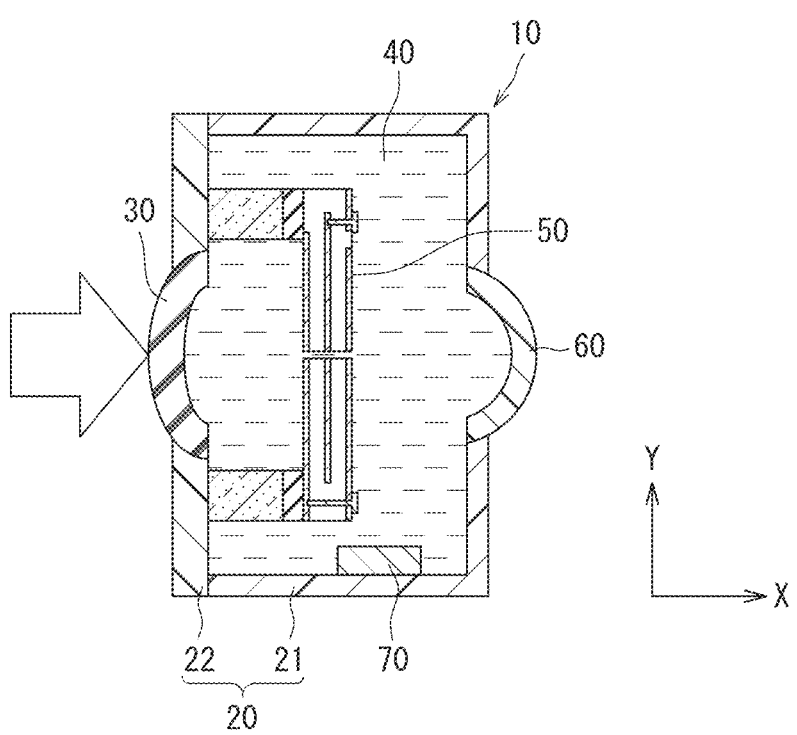
FIG. 11 is a cross-sectional view showing a biological sound detection device according to a fourth embodiment.

FIG. 11 shows a biological sound detection device 10 of the present embodiment. FIG. 11 shows a state in which the load of the occupant 110 is applied. In FIG. 11, for convenience, the occupant 110 and the seat 100 are omitted, and the load is indicated by a white arrow.

The biological sound detection device 10 shown in FIG. 11 further includes a sensor 70. Other configurations are similar to those of the biological sound detection device 10 described in the first embodiment. The sensor 70 is arranged in the housing 20. The sensor 70 is arranged in the accommodation region for the medium 40. The sensor 70 detects a physical quantity that correlates with the pressure of the medium 40. The sensor 70 of the present embodiment is a pressure sensor that detects the pressure of the medium 40. The sensor 70 is fixed to, for example, the case 21 of the housing 20. Since temperature is a physical quantity that correlates with pressure, a temperature sensor may be used instead of the pressure sensor.

Summary of Fourth Embodiment

When the pressure of the medium 40 changes, the frequency characteristics of the elements other than the medium 40, that is, the frequency characteristics of the entire hardware of the biological sound detection device 10 change. The biological sound detection device 10 of the present embodiment includes the sensor 70 that detects a physical quantity that correlates with the pressure of the medium 40. This configuration can correct the frequency characteristics according to the pressure of the medium 40 in the signal processing circuit in the subsequent stage. For example, the cutoff frequency of the filter may be corrected. For example, the frequency bandwidth of frequency conversion and reverse frequency conversion may be corrected. With this configuration, it is possible to further increase the detection sensitivity of the biological sound.

Further, the sensor 70 can detect whether or not the occupant 110 is seated on the seat 100. That is, the sensor 70 can also be used as a seating sensor.

The configuration including the sensor 70 is not limited to the combination with the first embodiment. Any of the second embodiment, the third embodiment, and the modifications can be combined.

Fifth Embodiment

The fifth embodiment is a modification of the preceding embodiments as a basic configuration and may incorporate description of the preceding embodiments.

A plurality of biological sound detection devices 10 having the configuration shown in the preceding embodiments may be arranged (mounted) in the moving object. The plurality of biological sound detection devices 10 are arranged in at least one of the seating portion 101, the backrest 102, and the seat belt 105 of the seat 100 of the moving object. For example, all the biological sound detection devices 10 may be arranged in the backrest 102. One of the biological sound detection devices 10 may be arranged in the backrest 102, and the other one may be arranged in the seat belt 105.

Figure 12:
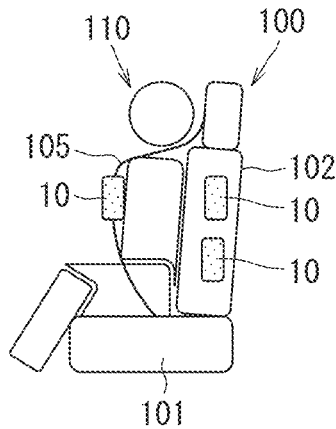
FIG. 12 is a diagram showing an arrangement of a biological sound detection device according to a fifth embodiment.

FIG. 12 shows an example of the arrangement of the biological sound detection devices 10. In FIG. 12, two biological sound detection devices 10 are arranged in the backrest 102, and one biological sound detection device 10 is arranged in the seat belt 105.

Summary of Fifth Embodiment

As described above, by arranging the plurality of biological sound detection devices 10, the sitting posture of the occupant 110 can also be detected. In addition, signal source estimation processing such as independent component analysis can be executed. As a result, even when noise (for example, respiratory sound) other than the detection target (for example, heart sound) is large, the detection target can be accurately detected.

Sixth Embodiment

The sixth embodiment is a modification of the preceding embodiments as a basic configuration and may incorporate description of the preceding embodiments.

Figure 13:
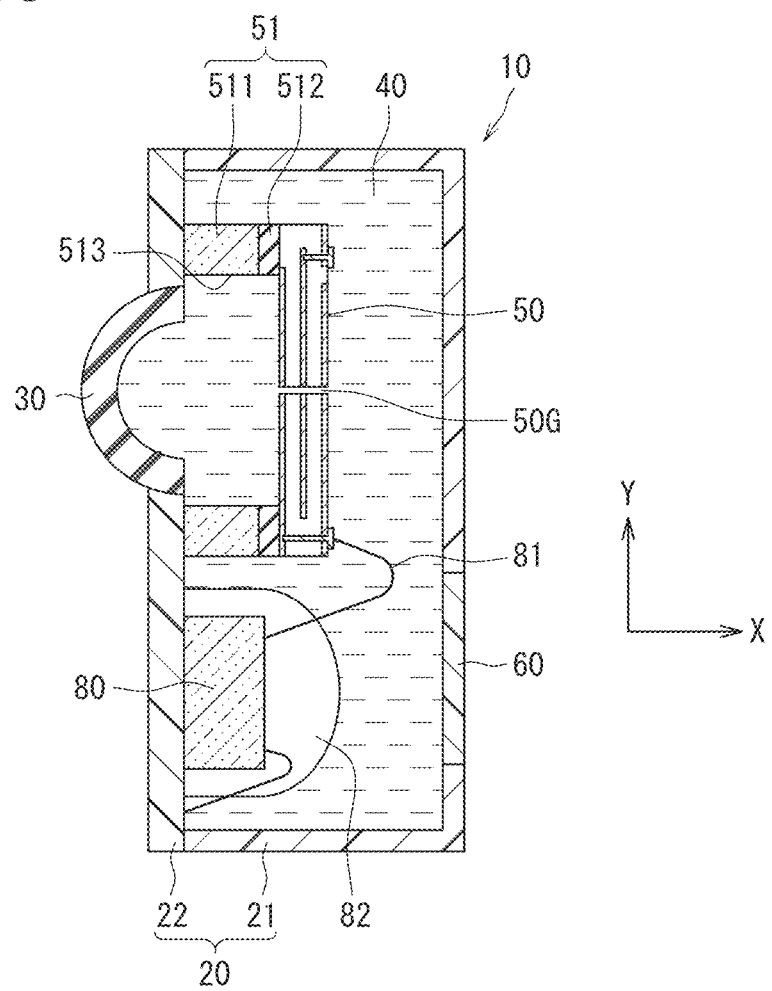
FIG. 13 is a cross-sectional view showing a biological sound detection device according to a sixth embodiment.

FIG. 13 shows a biological sound detection device 10 of the present embodiment. FIG. 13 shows a state in which the load of the occupant 110 is not applied. The biological sound detection device 10 further includes a signal processing circuit 80. The signal processing circuit 80 includes a circuit for processing the output signal of the transducer unit 50, for example, a filter circuit and the like. The signal processing circuit 80 may be provided as, for example, an IC chip, or may be provided by a plurality of electronic components. The signal processing circuit 80 is electrically connected to a pad of the transducer unit 50 via a wiring member 81 such as a bonding wire. The signal processing circuit 80 may be sealed by a sealing material 82. Other configurations are similar to those of the biological sound detection device 10 described in the first embodiment.

Summary of Sixth Embodiment

As described above, the biological sound detection device 10 may integrally include the signal processing circuit 80. The configuration including the signal processing circuit 80 is not limited to the combination with the first embodiment. Any of the second embodiment, the third embodiment, the fourth embodiment, the fifth embodiment, and the modifications can be combined.

Other Embodiments

The disclosure in this specification and drawings is not limited to the exemplified embodiments. The disclosure encompasses the illustrated embodiments and variations thereof by those skilled in the art. For example, the disclosure is not limited to the parts and/or combinations of elements shown in the embodiments. The disclosure may be implemented in various combinations. The disclosure may have additional parts that may be added to the embodiment. The disclosure encompasses omissions of parts and/or elements of the embodiments. The disclosure encompasses replacement or combination of parts and/or elements between one embodiment and another. The disclosed technical scope is not limited to the description of the embodiments. It should be understood that some disclosed technical ranges are indicated by description of claims, and includes every modification within the equivalent meaning and the scope of description of claims.

The disclosure in the specification, drawings and the like is not limited by the description of the claims. The disclosures in the specification, the drawings, and the like encompass the technical ideas described in the claims, and further extend to a wider variety of technical ideas than those in the claims. Therefore, various technical ideas can be extracted from the disclosure of the specification, the drawings and the like without being limited to the description of the claims.

When an element or a layer is described as "disposed above" or "connected", the element or the layer may be directly disposed above or connected to another element or another layer, or an intervening element or an intervening layer may be present therebetween. In contrast, when an element or a layer is described as "disposed directly above" or "directly connected", an intervening element or an intervening layer is not present. Other terms used to describe the relationships between elements (for example, "between" vs. "directly between", and "adjacent" vs. "directly adjacent") should be interpreted similarly. As used herein, the term "and/or" includes any combination and all combinations relating to one or more of the related listed items. For example, the term A and/or B includes only A, only B, or both A and B.

Spatial relative terms "inside", "outside", "back", "bottom", "low", "top", "high", etc. are used herein to facilitate the description that describes relationships between one element or feature and another element or feature. Spatial relative terms can be intended to include different orientations of a device in use or operation, in addition to the orientations depicted in the drawings. For example, when the device in the figure is flipped over, an element described as "below" or "directly below" another element or feature is directed "above" the other element or feature. Therefore, the term "below" can include both above and below. The device may be oriented in the other direction (rotated 90 degrees or in any other direction) and the spatially relative terms used herein are interpreted accordingly.

The application of the biological sound detection device 10 is not limited to the biological sound detection of the occupant 110 of the moving object. For example, the biological sound detection device 10 may be used for an electronic stethoscope or the like.

An example is shown in which each of the pressure adjusting units 60, 61, and 62, together with the housing 20 and the detection unit 30, provides the accommodation region for the medium 40, but the present disclosure is not limited thereto. For example, in order to suppress an increase in pressure of the medium 40 due to deformation of the detection unit 30, a through hole in the housing 20 may be provided. A part of the medium 40 may escape to the outside of the housing 20 through the through hole.

What is claimed is:

1. A biological sound detection device comprising:
    a housing;
    a medium having an acoustic impedance closer to water than air;
    a transducer unit that is arranged in the housing, and converts a biological sound transmitted through the medium into an electric signal;
    a detection unit that provides, together with the housing, an accommodation region that accommodates the medium, detects the biological sound, transmits the biological sound to the medium, and is deformable in a direction approaching the transducer unit according to a load of a physical body; and
    a pressure adjusting unit that adjusts a pressure of the medium so as to suppress an increase in the pressure of the medium due to deformation of the detection unit, wherein the pressure adjusting unit, together with the housing and the detection unit, provides the accommodation region, and the pressure adjusting unit expands the accommodation region so as to suppress the increase in the pressure of the medium, the pressure adjusting unit expands the accommodation region by deformation, and the pressure adjusting unit includes an air layer provided adjacently to the medium in the housing, and expands the accommodation region by reducing a volume of the air layer.

2. The biological sound detection device according to claim 1, further comprising a sensor that detects a physical quantity that correlates with the pressure of the medium.

3. The biological sound detection device according to claim 1, wherein the physical body is an occupant in a moving object, and the biological sound detection device is arranged in at least one of a backrest, a seating portion, and a seat belt of a seat on which the occupant sits.

\* \* \* \* \*